United States Patent

Köppe et al.

[11] 4,021,576
[45] May 3, 1977

[54] PHARMACEUTICAL COMPOSITIONS CONTAINING A 1-(2'-ETHYNYL-PHENOXY)-2-HYDROXY-3-(CYCLOALKYL-AMINO)-PROPANE AND METHOD OF USE

[75] Inventors: Herbert Köppe; Werner Kummer; Helmut Stähle; Karl Zeile, all of Ingelheim am Rhein; Albrecht Engelhardt, Mainz; Werner Taunecker, Munster-Sarmsheim, all of Germany

[73] Assignee: Boehringer Ingelheim GmbH, Ingelheim am Rhein, Germany

[22] Filed: Dec. 10, 1975

[21] Appl. No.: 639,342

Related U.S. Application Data

[60] Division of Ser. No. 310,638, Nov. 29, 1972, Pat. No. 3,937,706, which is a continuation-in-part of Ser. No. 57,353, July 22, 1970, Pat. No. 3,755,413.

[30] Foreign Application Priority Data

July 23, 1969  Germany .................. 1937477

[52] U.S. Cl. .................................. 424/330
[51] Int. Cl.² .......................... A61K 31/135

[58] Field of Search .............. 424/330, 316

[56] References Cited

UNITED STATES PATENTS

| 3,590,084 | 6/1971 | Peperkamp et al. | 260/570.7 |
| 3,755,413 | 8/1973 | Koppe et al. | 424/330 |

*Primary Examiner*—Albert T. Meyers
*Assistant Examiner*—Daren M. Stephens
*Attorney, Agent, or Firm*—Hammond & Littell

[57] ABSTRACT

Pharmaceutical compositions containing as an active ingredient a compound of the formula

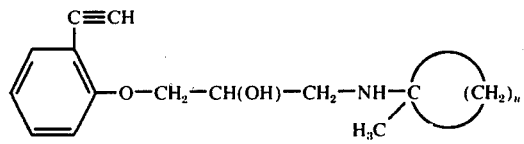

wherein $n$ is 4 or 5, or a non-toxic, pharmacologically acceptable acid addition salt thereof; and a method of using the same as β-adrenergic receptor blockers.

6 Claims, No Drawings

PHARMACEUTICAL COMPOSITIONS CONTAINING A 1-(2'-ETHYNYL-PHENOXY)-2-HYDROXY-3-(CYCLOALKYL-AMINO)-PROPANE AND METHOD OF USE

This is a division of copending application Ser. No. 310,638 filed Nov. 29, 1972, now U.S. Pat. No. 3,937,706; which in turn is a continuation-in-part of application Ser. No. 57,353 filed July 22, 1970, now U.S. Pat. No. 3,755,413.

This invention relates to novel pharmaceutical compositions containing a 1-(2'-ethynyl-phenoxy)-2-hydroxy-3-(cycloalkyl-amino)-propane or a non-toxic acid addition salt thereof, as well as to a method of using the same as β-adrenergic receptor blockers.

More particularly, the present invention relates to pharmaceutical dosage unit compositions containing as an active ingredient a compound of the formula

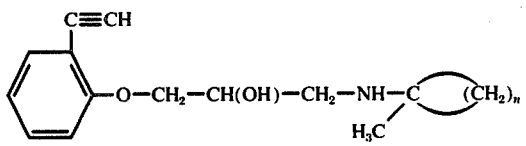

wherein n is 4 or 5, or a non-toxic, pharmacologically acceptable acid addition salt thereof.

The compounds embraced by formula I may be prepared by reacting the epoxide of the formula

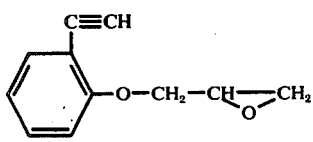

with a cycloalkylamine of the formula

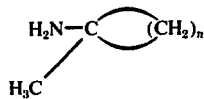

wherein n has the same meanings as in formula I.

The starting compounds of the formulas II and III are known compounds and may be prepared by conventional methods.

The compounds of the formula I comprise an asymmetric carbon atom in the CHOH-group and therefore occur as racemates as well as in the form of optical antipodes. The latter may be obtained by means of separation of racemates with the usual auxiliary acids, such as dibenzoyl-D-tartaric acid or D-3-bromo-camphor-8-sulfonic acid.

The 1-phenoxy-3-cycloalkylamino-propanols of the formula I may be converted into non-toxic, pharmaceutically acceptable acid addition salts in conventional fashion. Examples of such salts are, for instance, those formed with hydrochloric acid, hydrobromic acid, sulfuric acid, methanesulfonic acid, maleic acid, acetic acid, oxalic acid, lactic acid, tartaric acid, 8-chloro-theophylline or the like.

The following examples illustrate the preparation of compounds of the formula I and non-toxic, pharmacologically acceptable acid addition salts thereof.

EXAMPLE 1

1-(2'-Ethynyl-phenoxy)-2-hydroxy-3-[(1''-methyl-cyclopentyl)-amino]-propane and its hydrochloride 7.5 gm (0.04 mol) of 1-(2'-ethynyl-phenoxy)-2,3-epoxypropane were dissolved in 80 ml of ethanol, 5 gm (0.05 mol) of (1-methyl-cyclopentyl)-amine were added, and the mixture was refluxed for 2.5 hours. The residue remaining after distilling off the solvent, 1-(2'-ethynyl-phenoxy)-2-hydroxy-3-[(1''-methyl-cyclopentyl)-amino]-propane, was dissolved in ethanol, and ethereal HCl was added. The colorless crystalline precipitate was recrystallized from ethanol/ether, yielding 6.7 gm of the hydrochloride of the formula

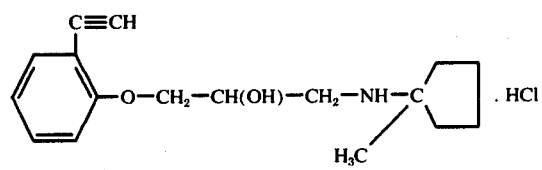

which had a melting point of 171°–173° C.

EXAMPLE 2

Using a procedure analogous to that described in Example 1, 1-(2'-ethynyl-phenoxy)-2-hydroxy-3-[(1''-methyl-cyclohexyl)-amino]-propane and its hydrochloride, m.p. 184°–185° C, of the formula

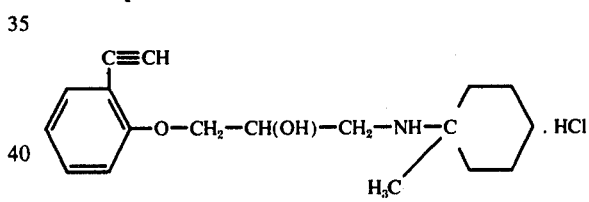

were prepared from 1-(2'-ethynyl-phenoxy)-2,3-epoxy-propane and (1-methyl-cyclohexyl)-amine.

The compounds embraced by formula I above and their non-toxic, pharmacologically acceptable acid addition salts have useful pharmacodynamic properties. More particularly, they exhibit very effective β-adrenergic receptor blocking activities in warm-blooded animals, such as guinea pigs, and are therefore useful therapeutics for the treatment of prophylaxis of diseases of the coronaries and for the treatment of cardiac arrythmia, especially tachycardia. The compounds also exhibit effective hypotensive activities.

For pharmaceutical purposes the compounds of the formula I or their non-toxic acid addition salts are administered to warm-blooded animals perorally or parenterally as active ingredients in customary dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. Such dosage unit compositions may, in addition to a compound of the present invention, also comprise an effective dosage unit of one or more compounds having a different pharmacodynamic property, such as a coronary dilator, a sympathomimetic, a cardiac glycoside and/or a tranquilizer. One effective dosage unit of the compounds of the formula I or their non-toxic acid addition salts is from 0.0166 to 5.0 mgm/kg body weight, preferably 0.083 to 1.67 mgm/kg (perorally) and 0.0166 to 0.34 mgm/kg (parenterally).

The following examples illustrate a few dosage unit compositions comprising a compound of the formula I or a non-toxic acid addition salt thereof as an active ingredient and represent the best mode contemplated of putting the invention into practical use. The parts are parts by weight unless otherwise specified.

EXAMPLE 3

Tablets

The tablet composition was compounded from the following ingredients:

| | |
|---|---|
| 1-(2'-Ethynyl-phenoxy)-2-hydroxy-3-[(1''-methyl-cyclopentyl)-amino]-propane . HCl | 40.0 parts |
| Corn starch | 164.0 parts |
| Secondary calcium phosphate | 240.0 parts |
| Magnesium stearate | 1.0 parts |
| Total | 445.0 parts |

Preparation

The individual components were intimately admixed with each other, the mixture was granulated in customary fashion, and the granulate was compressed into 445 mgm tablets with a conventional tablet making machine. Each tablet contained 40 mgm of the propanol salt and, when administered perorally to a warm-blooded animal of about 60 kg body weight in need of such treatment, produced a very effective $\beta$-adrenergic receptor blocking action.

EXAMPLE 4

Gelatin Capsules

The capsule filler composition was compounded from the following ingredients:

| | |
|---|---|
| 1-(2'-Ethynyl-phenoxy)-2-hydroxy-3-[(1''-methyl-cyclohexyl)-amino]-propane . HCl | 25.0 parts |
| Corn starch | 175.0 parts |
| Total | 200.0 parts |

Preparation

The components were intimately admixed with each other, and 200 mgm-portions of the mixture were filled into gelatin capsules of suitable size. Each capsule contained 25 mgm of the propanol salt and, when perorally administered to a warm-blooded animal of about 60 kg body weight in need of such treatment, produced a very effective $\beta$-adrenergic receptor blocking action.

EXAMPLE 5

Hypodermic Solution

The solution was compounded from the following ingredients:

| | | |
|---|---|---|
| 1-(2'-Ethynyl-phenoxy)-2-hydroxy-3-[(1''-methyl-cyclopentyl)-amino]-propane . HCl | | 2.5 parts |
| Sodium salt of EDTA (ethylenediamine-tetraacetic acid) | | 0.2 parts |
| Distilled water | q.s.ad | 100.0 parts |

Preparation

The propanol salt and the EDTA salt were dissolved in a sufficient amount of distilled water, and the solution was diluted to the desired volume with distilled water. The solution was filtered until free from suspended particles and filled into 1 cc ampules under aseptic conditions. Finally, the ampules were sterilized and sealed. Each ampule contained 25 mgm of the propanol salt, and when the contents thereof were intravenously administered to a warm-blooded animal of about 60 kg body weight in need of such treatment, a very effective $\beta$-adrenergic receptor blocking action was produced.

EXAMPLE 6

Coated Sustained Release Tablets

The tablet core composition was compounded from the following ingredients:

| | | |
|---|---|---|
| 1-(2'-Ethynyl-phenoxy)-2-hydroxy-3-[(1''-methyl-cyclopentyl-amino]-propane . HCl | | 25.0 parts |
| Carboxymethyl cellulose (CMC) | | 295.0 parts |
| Stearic acid | | 20.0 parts |
| Cellulose acetate phthalate (CAP) | | 40.0 parts |
| | Total | 380.0 parts |

Preparation

The propanol salt, the CMC and the stearic acid were intimately admixed with each other, and the mixture was granulated in customary fashion, using a solution of the CAP in 200 ml of a mixture of ethanol and ethylacetate as the moistening agent. The granulate was then compressed into 380 mgm cores, which were coated in the usual way with an aqueous 5% solution of polyvinylpyrrolidone containing sugar. Each coated tablet contained 25 mgm of the propanol salt and, when administered perorally to a warm-blooded animal of about 60 kg body weight in need of such treatment, produced a very effective $\beta$-adrenergic receptor blocking action over an extended period of time.

EXAMPLE 7

Tablets with combination of active ingredients

The tablet composition was compounded from the following ingredients:

| | |
|---|---|
| 1-(2'-Ethynyl-phenoxy)-2-hydroxy-3-[(1''-methyl-cyclohexyl)-amino]-propane . HCl | 35.0 parts |
| 2,6-Bis-(diethanolamino)-4,8-dipiperidino-pyrimido-[5,4-]pyrimidine | 75.0 parts |
| Lactose | 164.0 parts |
| Corn starch | 194.0 parts |
| Colloidal silicic acid | 14.0 parts |
| Polyvinylpyrrolidone | 6.0 parts |
| Magnesium stearate | 2.0 parts |
| Soluble starch | 10.0 parts |

|        |       |            |
|--------|-------|------------|
|        | Total | 500.0 parts |

Preparation

The propanol salt, the lactose, the corn starch, the colloidal silicic acid and the polyvinylpyrrolidone were intimately admixed with each other, and the mixture was granulated in the usual way, using an aqueous solution of the soluble starch as the moistening agent. The granulate was admixed with magnesium stearate, and the composition was compressed into 500 mgm-tablets. Each tablet contained 35 mgm of the propanol salt and 75 mgm of the pyrimmido-pyrimidine compound and, when perorally administered to a warm-blooded animal of about 60 kg body weight in need of such treatment, produced very effective β-adrenergic receptor blocking and coronary dilating actions.

Analogous results were obtained when any one of the other compounds embraced by formula I or a non-toxic acid addition salt thereof was substituted for the particular propanol salt in Examples 3 through 7. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A pharmaceutical dosage unit composition consisting essentially of an inert pharmaceutical carrier and an effective β-adrenolytic amount of the compound of the formula

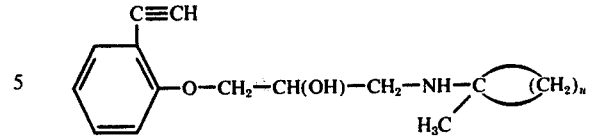

wherein $n$ is 4 or 5, or a non-toxic, pharmacologically acceptable acid addition salt thereof.

2. A composition of claim 1, wherein said compound is 1-(2'-ethynyl-phenoxy)-2-hydroxy-3-[1''-methyl-cyclopentyl)-amino]-propane or a non-toxic, pharmacologically acceptable acid addition salt thereof.

3. A composition of claim 1, wherein said compound is 1-(2'-ethynyl-phenoxy)-2-hydroxy-3-[(1''-methyl-cyclohexyl)-amino]-propane or a non-toxic, pharmacologically acceptable acid addition salt thereof.

4. The method of blocking β-adrenergic receptors in a warm-blooded animal in need of such treatment, which comprises administering to said animal an effective β-adrenolytic amount of a compound of the formula

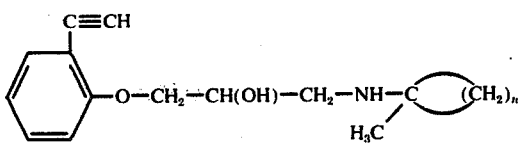

wherein $n$ is 4 or 5, or a non-toxic, pharmacologically acceptable acid addition salt thereof.

5. The method of claim 4, wherein said compound is 1-(2'-ethynyl-phenoxy)-2-hydroxy-3-[(1''-methyl-cyclopentyl)-amino]-propane or a non-toxic, pharmacologically acceptable acid addition salt thereof.

6. The method of claim 4, wherein said compound is 1-(2'-ethynyl-phenoxy)-2-hydroxy-3-[(1''-methyl-cyclohexyl)-amino]-propane or a non-toxic, pharmacologically acceptable acid addition salt thereof.

* * * * *